United States Patent
Budaraju et al.

(10) Patent No.: US 10,221,386 B2
(45) Date of Patent: Mar. 5, 2019

(54) SYSTEM AND METHOD FOR CONTROLLING A FERMENTATION PROCESS

(75) Inventors: Srinivas Budaraju, Austin, TX (US); James F. Bartee, Stilesville, IN (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 829 days.

(21) Appl. No.: 12/889,142

(22) Filed: Sep. 23, 2010

(65) Prior Publication Data
US 2012/0077244 A1   Mar. 29, 2012

(51) Int. Cl.
   *C12P 7/06*   (2006.01)
   *C12N 1/16*   (2006.01)
   *C12M 1/36*   (2006.01)
   *C12M 1/00*   (2006.01)

(52) U.S. Cl.
   CPC ............ *C12M 41/48* (2013.01); *C12M 23/58* (2013.01); *C12N 1/16* (2013.01); *C12P 7/06* (2013.01); *Y02E 50/17* (2013.01)

(58) Field of Classification Search
   CPC ......... C12M 41/48; C12M 23/58; C12N 1/16; C12P 7/06
   See application file for complete search history.

(56) References Cited

U.S. PATENT DOCUMENTS

| 4,186,252 A   * | 1/1980 | Silhankova ............... 435/120 |
| 2008/0108048 A1 | 5/2008 | Bartee et al. |
| 2008/0167852 A1 | 7/2008 | Bartee et al. |
| 2009/0017164 A1 * | 1/2009 | Schisler et al. ............. 426/62 |

OTHER PUBLICATIONS

U.S. Appl. No. 12/771,496, filed Apr. 30, 2010, Srinivas Budaraju, et al.
"Nalco 3D TRASAR® Yeast Activity Monitor Enables Corn Ethanol Plants to Effectively Monitor Yeast during Propagation and Fermentation," http://www.nalco.com/documents/CH_872.pdf; 4 pages (Jan. 2009).

* cited by examiner

*Primary Examiner* — Kara D Johnson
(74) *Attorney, Agent, or Firm* — Fletcher Yoder, P.C.

(57) ABSTRACT

A method for controlling a fermentation process includes injecting a mash into a fermenter and injecting a liquid ammonia additive into the fermenter. The liquid ammonia additive is injected in a closed-loop manner. The method may be used to control the fermentation processes of one or more fermenters operating in parallel.

20 Claims, 4 Drawing Sheets

SYSTEM AND METHOD FOR CONTROLLING A FERMENTATION PROCESS

BACKGROUND

The invention relates generally to control systems, and more particularly to process control employing novel techniques for controlling the fermentation process of a biofuel production plant.

A biofuel production plant may include one or more batch processes. One such batch process is the fermentation of a starch source to produce ethanol and other by-products in the presence of yeast and other enzymes in fermenters. A source of nitrogen may also be added to the fermenters to serve as a nutrient for the yeast. A process controller may be used to control certain variables of the fermentation process to achieve specified goals, such as maximizing ethanol production and/or maintaining yeast health. Existing methods of controlling the fermentation process may suffer from disadvantages that may result in decreased ethanol production, inefficient use of yeast, and longer turnaround times for the batch processes.

BRIEF DESCRIPTION

The present invention provides novel techniques for controlling the fermentation process of a biofuel production plant. In particular, the present techniques are presented in the context of a series of parallel fermenters of the biofuel production plant. More particularly, in various embodiments, the series of parallel fermenters may be coupled to a yeast additive system, an ammonia additive system, or both. However, it should be borne in mind that the invention may be applied in a wide range of contexts, in a variety of plants, and in any desired industrial, commercial, private, or other setting.

In accordance with one aspect of the present disclosure, a method for controlling a fermentation process includes injecting a mash into a fermenter and injecting a liquid ammonia additive into the fermenter. The liquid ammonia additive is injected in a closed-loop manner.

In accordance with another aspect, a method for controlling a fermentation process includes injecting a mash into a fermenter and injecting a liquid ammonia additive into the fermenter. The liquid ammonia additive is injected in a closed-loop manner as a function of volumetric, mass or percentage fill of mash in the fermenter. Finally, the method includes injecting a liquid yeast additive into the fermenter.

In accordance with a further aspect, a system for controlling a fermentation process includes a fermenter configured to receive mash and to ferment the mash during a batch process, a liquid ammonia additive system configured to inject liquid ammonia additive into the fermenter, and a control system coupled to the liquid ammonia additive system and configured to regulate injection of liquid ammonia additive into the fermenter in a closed-loop manner.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Incorporation by Reference

The following references are hereby incorporated by reference in their entirety as though fully and completely set forth herein:

U.S. patent application Ser. No. 11/927,960 titled "Nonlinear Model Predictive Control of a Biofuel Fermentation Process" filed Oct. 30, 2007;

U.S. patent application Ser. No. 11/928,344 titled "Model Predictive Control of Fermentation Temperature in Biofuel Production" filed Oct. 30, 2007; and U.S. patent application Ser. No. 12/771,496 titled "Yeast Growth Maximization with Feedback for Optimal Control of Filled Batch Fermentation in a Biofuel Manufacturing Facility" filed Apr. 30, 2010.

Figure 1:
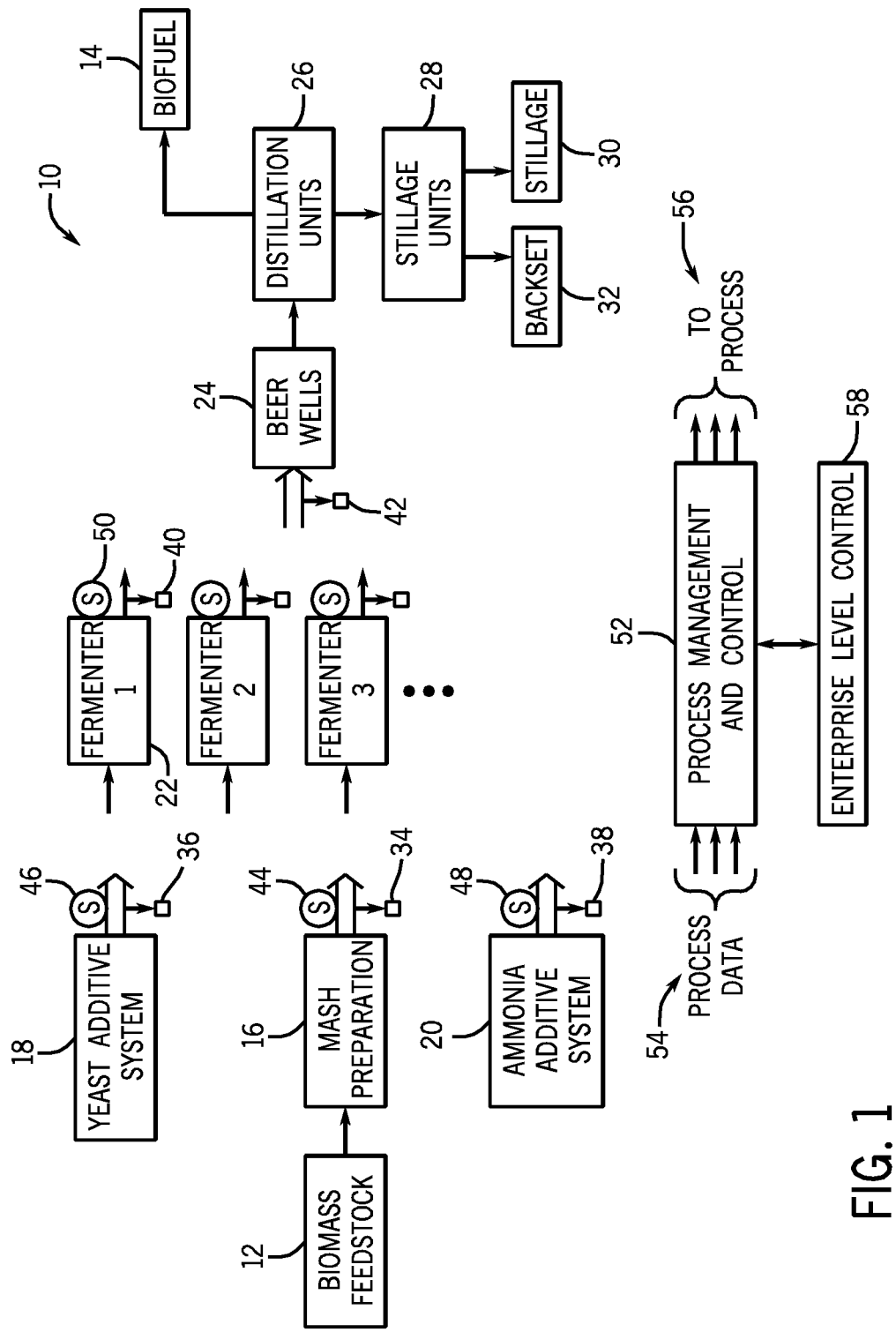
FIG. 1 is a diagrammatical representation of an exemplary biofuel production plant.

FIG. 1 is a diagram of an exemplary biofuel production plant 10 illustrating how biomass feedstock 12 may be processed through several stages to produce biofuel 14. For example, the biofuel production plant 10 may be a dry mill ethanol facility that produces ethanol from corn by grinding corn kernels into flour and then forming a slurry or mash by adding water, enzymes, yeast, nutrients, and/or other additives. Although the following discussion pertains to dry mill facilities, certain embodiments may also be applicable to wet mill ethanol facilities that produce ethanol by soaking corn in sulfuric acid and water prior to grinding. Returning to FIG. 1, one or more of the various stages in the biofuel production plant 10 may be susceptible to exemplary methods of controlling a fermentation process in a closed-loop manner, as described in detail below. In FIG. 1, biomass 12 may first be provided to a mash preparation process 16, where water (which may include recycled water) may be added and the biomass 12 may be broken down to increase the surface area-to-volume ratio. This increase in surface area may allow for sufficient interaction of the water and biomass 12 surface area to achieve a solution of fermentable sugars in water. For example, the starch included in corn may be converted into sugars, such as glucose, using enzymes. The mixture, a biomass 12 and water slurry, may be cooked to promote an increase in the amount of contact between the biomass 12 and water in solution and to increase the separation of carbohydrate biomass from non-carbohydrate biomass. The output of the mash preparation process 16 (i.e., the fermentation feed or mash) is then be sent to a fermentation process, where one or more fermenters 22 operate to ferment the biomass/water mash produced by the mash preparation process 16.

In the fermenters 22, yeast, enzymes, and nutrients are used to convert the biomass 12 into a biofuel 14 and by-products, such as carbon dioxide, water, and non-fermentable biomass (solids). In certain embodiments, the ammonia is stored in an ammonia additive system 20 prior to injection into the fermenters 22. In some embodiments, the ammonia additive system 20 may store anhydrous ammonia, which is ammonia essentially free of water.

Aqueous ammonia is a solution of ammonia in water and may be used in other embodiments. Ammonia is a source of nitrogen, and thus, may serve as a nutrient for the yeast. In addition, ammonia may be used to control the pH of a fermenter batch. Ammonia may posses several advantages compared to other nitrogen sources that may be used in the fermenters 22, such as urea. For example, ammonia may be transferred immediately from a storage tank to the fermenters 22. In addition, ammonia may be easily transported via piping and pumps because it is a liquid under normal conditions. However, urea may be packaged in bags and be manually added to the fermenters 22. Furthermore, the addition of ammonia may be precisely controlled using flow meters and flow controllers. Urea may be added to the fermenters 22 one bag at a time, which may result in variability between batches. Finally, ammonia may be less expensive than urea. Thus, the various advantages of ammonia may enable the fermentation process to be more easily and economically controlled than by using other nitrogen sources, such as urea. In the discussion that follows, the term "ammonia" may be used to refer to anhydrous ammonia, aqueous ammonia, or any other type of ammonia in liquid form.

In other embodiments, a yeast additive system 18 may store yeast to be used in the fermenters 22. In other words, some embodiments may include both the yeast additive system 18 and the ammonia additive system 20 and other embodiments may include only the ammonia additive system 20 or the yeast additive system 18. When included, one type of yeast that may be used in the fermenters 22 is cream yeast, which is a suspension of live yeast cells in a liquid, siphoned off from growth medium. Cream yeast may posses several advantages compared to other types of yeast that may be used in the fermenters 22, such as dry yeast. For example, cream yeast may be transferred immediately from a storage tank to the fermenters 22 whenever the cream yeast is needed during fermentation. However, preparation of dry yeast in a propagation tank is a batch process that may last for 7 to 8 hours, for example. Therefore, preparation of dry yeast is initiated several hours prior to addition to the fermenters 22. In addition, using the propagation tank means that dry yeast is introduced only during a fill cycle and thus, only once during a fermenter batch. Cream yeast may be metered into the fermenter 22 at any point during a fermenter batch and at any desired flow rate. Further, the use of cream yeast may reduce fermentation variability because cream yeast is not prepared in a propagation tank prior to use. Because of other activities in the biofuel production plant 10, an operator may not be able to prepare each propagation tank of dry yeast in the same way and/or with the same batch time. The resulting variability of dry yeast in the propagation tank may introduce variability into the fermentation process. In addition, inadequate cleaning of the propagation tank may affect the rest of the biofuel production plant 10. Moreover, cream yeast may be easily transported via piping and pumps because of its slurry-like properties. Dry yeast may be packaged in bags and be manually added to the propagation tank, which is a labor-intensive process. Furthermore, the addition of cream yeast may be precisely controlled using flow meters and flow controllers. Thus, the various advantages of cream yeast may enable the effect of the yeast on the fermentation process to be more easily controlled than by using other types of yeast, such as dry yeast. In the discussion that follows, the term "yeast" may be used to refer to cream yeast or any other type of propagated yeast in liquid form.

As discussed above, certain embodiments may include only the ammonia additive system 20 or the yeast additive system 18. For example, in certain embodiments that include the ammonia additive system 20, dry yeast may be added to the fermenters 22. In other embodiments that include the yeast additive system 18, urea may be used as a nutrient for the yeast in the fermenters 22.

The glucose produced in the mash preparation process 16 may be converted into ethanol in the presence of yeast during fermentation. Heat generated by fermentation is removed by one or more coolers. The fermentation process is a batch process and may include multiple fermenters 22 operating in parallel (indicated by the vertical ellipsis). Depending upon the plant design and the number of fermenters, the batch start times may be staggered in order to optimize the utilization of the capacity of beer wells 24 and smoothly distribute the flow of fermentation feed to the fermentation process and the flow of biofuel 14 and stillage as output from the fermentation process.

After being temporarily stored in the beer wells 24, the output from the fermenters 22 may be sent to a distillation process, e.g., one or more distillation units 26, to separate biofuel 14 from water and other liquid constituents, carbon dioxide, and non-fermentable solids. If the biofuel 14 has to be dehydrated to moisture levels less than 5% by volume, the biofuel 14 may be processed through a processing unit that may include a molecular sieve or similar processing equipment, separators, filters and so forth. The finished biofuel 14 may then be processed, such as by denaturing to render it unfit for human consumption.

The distillation units 26 separate the biofuel 14 from water and other liquids. Water may be used in the form of steam for heat and separation, and the condensed water may be recycled back to the mash preparation process 16. Stillage 30 (non-fermentable solids and yeast residue), the heaviest output of the distillation units 24, may be sent to stillage processing units 28 for further development of co-products from the biofuel 14 production process.

The stillage processing units 28 may separate additional water and ethanol from the cake solids, and may recycle the water, referred to as backset 32, back to the mash preparation process 16. The backset 32 may include both dissolved and suspended solids. Several stillage processing options may be utilized, including: (1) selling the stillage with minimal processing and (2) further processing the stillage by separating moisture from the solid products via one or more centrifuge units. Following the centrifuge units, the non-fermentable solids may be transported to dryers for further moisture removal. A portion of the stillage liquid (concentrate) may also be recycled back to the fermenters 22. However, the bulk of the flow may generally be sent to evaporator units, where more liquid may be separated from the liquid stream, causing the liquid stream to concentrate into a syrup, while solid stillage may be sent to a drying process, e.g., using a drying unit or evaporator, to dry the solid stillage to a specified water content. The syrup may then be sent to a syrup tank. Syrup in inventory may be processed using a number of options. For instance, the syrup may be: (1) sprayed in dryers to achieve a specified color or moisture content, (2) added to the partially dried stillage product, or (3) sold as a separate liquid product. The evaporator units may have a water by-product stream that is recycled back to the mash preparation process 16.

A number of sample points may be provided throughout the biofuel production plant 10 where samples may be drawn for analysis. Results of the analysis of the samples may be used in the exemplary methods of controlling the fermentation process as described in detail below. As some of these samples may already be routinely obtained, the exemplary methods may make use of the existing sample results without increasing laboratory workload. Several samples that may be included in certain embodiments are described below. For example, a mash preparation sample 34 may be used to determine physical properties and compositional data of the mash. Next, a yeast additive system sample 36 may be used to determine the concentration and activity of the yeast. An ammonia additive system sample 38 may be used to determine the concentration of the ammonia. Fermenter samples 40 may be taken periodically during fermenter batches to determine concentrations of fermentation products, such as, but not limited to, ethanol, succinic acid, lactic acid, glycerol, and acetic acid. After the fermenter batch is complete, a fermenter drop sample 42 may be used to determine the final concentrations of the same components. Other embodiments of the biofuel production plant 10 may omit some of these samples or include additional samples.

In particular embodiments, a variety of sensors, or process instruments, may be placed throughout the biofuel production plant 10. Such sensors may measure process data or operating variables, such as, but not limited to, temperatures, flow rates, pressures, liquid levels, or pH values, of various streams, vessels, or equipment of the biofuel production plant 10. Other sensors may be on-line analyzers capable of determining real time or near real time compositional data of streams. Where available, one or more sensors may even be capable of determining yeast activity. In addition to sensors, the operating variables may also be determined using inferential models, laboratory values (as discussed above), or combinations thereof. Several sensors that may be included in certain embodiments are described below. For example, a mash preparation sensor 44 may be used to measure the flow rate or compositional data of the mash. Next, a yeast additive system sensor 46 may be used to determine the flow rate or activity of the yeast. An ammonia additive system sensor 48 may be used to determine the flow rate of the ammonia. Fermenter sensors 50 may be used to determine compositional data, liquid levels, temperatures, pH values, and so forth. Other embodiments of the biofuel production plant 10 may omit some of these samples or include additional samples.

Sensor output 54 may be transmitted to a process management and control module 52. Plant operators may be able to monitor the sensor output 54 and interact with the control system 52 to provide new set points, for example. Based on sensor output 54, input from operators, programming, and/or other inputs, the module 52 transmits output signals 56 to the process. Thus, the module 52 may operate in a closed-loop manner. The output signals 56 may be used to manipulate equipment, such as valves, motors, and/or pumps. For example, the output signals 56 may be used to adjust the flow rates of the yeast and/or ammonia. In addition, the module 52 may send process information to an enterprise level control module 58, which may be used to manage all information and functions of a business. The enterprise level control module 58 may also be referred to as an enterprise analyzer. Such modules may include computer systems located on-site at the production facility, or off-site, typically coupled to the facility via remote networking components and links. Such enterprise analysis may permit the coordination of production, maintenance, scheduling of delivery of needed materials (e.g., yeast and/or ammonia) and so forth.

Figure 2:
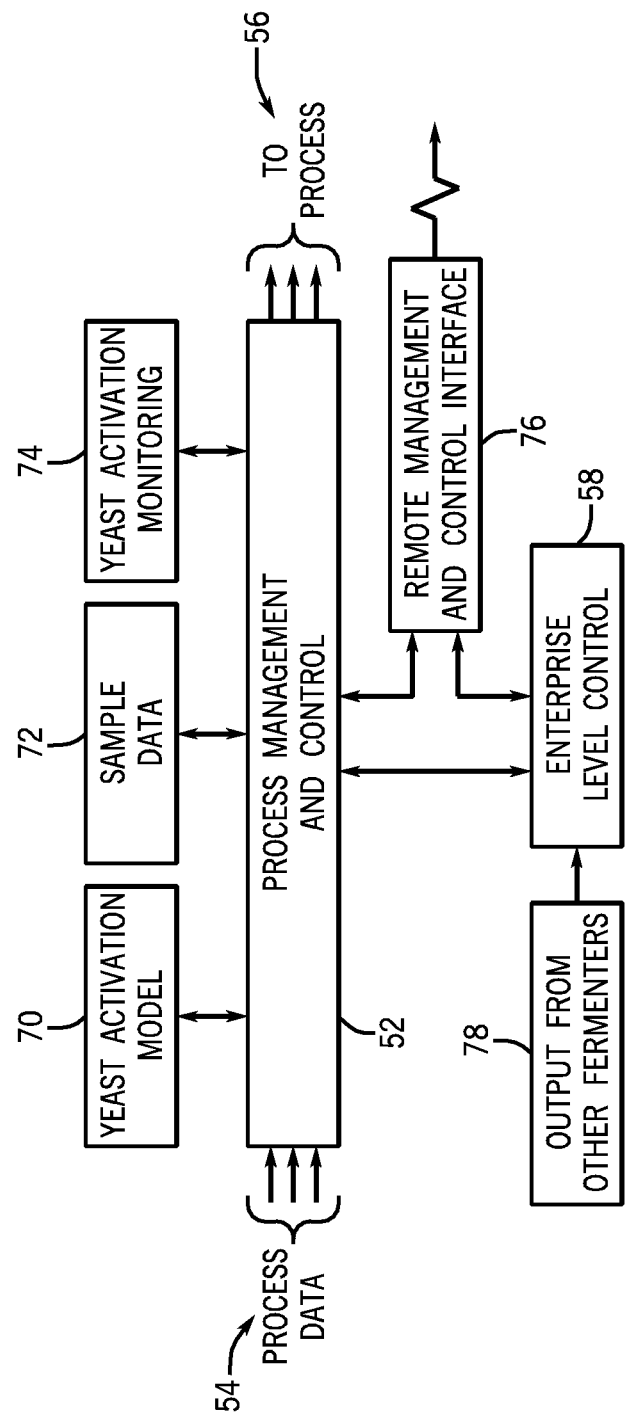
FIG. 2 is a diagrammatical representation of an exemplary control system capable of implementing an exemplary method of controlling a fermentation process.

FIG. 2 is a diagram of the process management and control module 52 capable of implementing an exemplary method of controlling a fermentation process. In certain embodiments, a yeast activation model 70 may provide a prediction of yeast activity to the module 52. Specifically, the yeast activation model 70 may be based on empirical models, inferential models, laboratory data, data obtained during fermenter batches, and so forth, as described more fully in U.S. patent application Ser. No. 11/927,960, incorporated by reference herein. The module 52 may send process data, such as, but not limited to, fermenter 22 temperature, pH value, fermentation time, mash properties, yeast properties, and ammonia properties to the yeast activation model 70. Using this information, the yeast activation model 70 may be able to predict the current activity of the yeast in the fermenter 22 and send this information to the module 52. If the yeast activity is lower than a threshold, the module 52 may transmit output signals 56 to appropriate equipment in an effort to increase (or more generally to control) yeast activity. For example, the flow rate of yeast to the fermenter 22 may be increased. Similarly, if the yeast activity is higher than a threshold, the module 52 may transmit output signals 56 to appropriate equipment in an effort to decrease yeast activity. For example, the flow rate of yeast to the fermenter 22 may be decreased.

In other embodiments, sample data 72 may be transmitted to the module 52. For example, a sample may be delivered to a laboratory, which may be an on-site laboratory, an in-process analyzer, or an off-site laboratory. A variety of standard laboratory methods may be used for the analysis of the sample, including high performance liquid chromatography (HPLC) and pH analysis, which may be commonly available on-site at biofuel production plants 10. The output from these methods will be raw results, which may include a chromatogram, a list of percent composition of various components, and/or pH values. The raw results may then be subject to further analysis, which may include processing the raw results to determine additional parameters or reformatting the raw results in a more useful configuration. The resulting sample data 72 may be sent directly to the module 52. Alternatively, plant operators may input the results manually. With either method of input, the sample data 72 may be used by the module 58 to perform the exemplary methods of controlling the fermenter process as described in detail below. For example, the results of the fermenter sample 40 may indicate that the concentration of ethanol is less than expected. Based on this information, the module 52 may transmit output signals 56 to appropriate equipment in an effort to adjust the fermentation process accordingly. For example, the flow rate of yeast and/or ammonia to the fermenter 22 may be increased. In addition, the module 52 may send a signal back to the sample data 72 to request additional or more frequent samples to be taken until ethanol production is back to normal.

In further embodiments, yeast activation monitoring 74 may provide an estimate of yeast activity to the module 52, as described more fully in U.S. patent application Ser. No. 12/771,496, incorporated by reference herein. Specifically, yeast activation monitoring 74 may include laboratory methods, such as, but not limited to, microscopic yeast cell counting and viability assessment by methylene blue staining of process samples. Another method involves adding chemicals to cause the yeast cells to fluoresce and quantifying the number of yeast cells using a fluorometer. The module 52 may also send additional process data to yeast activation monitoring 74. The yeast activation monitoring 74 may be able to determine the yeast characteristics of the sample and transmit this information to the module 52. Based on the monitored yeast activity results, the module 52 may transmit appropriate output signals 56 to the necessary equipment of the biofuel production plant 10.

As described above, the module 52 may send process information to the enterprise level control module 58. In certain embodiments, the enterprise level control module 58 may receive output from one or more of the yeast activation model 70, sample data 72, or yeast activation monitoring 74 directly, instead of through the process management and control module 52. Furthermore, information may be shared between a remote management and control interface 76 and both the process management and control module 52 and enterprise level control module 58. The interface 76 enables operators, engineers, and/or management at a remote location to monitor and/or interact with both the process management and control module 52 and enterprise level control module 58. Finally, the enterprise level control module 58 may receive output 78 from other disparate fermenters 22 of the same or different biofuel production plants 10. The enterprise level control module 58 may perform comparisons using the output mentioned above and the other output 78 to determine performance outputs associated with such comparisons. Such performance outputs may then be used to adjust the operation of the fermenter 22.

Figure 3:
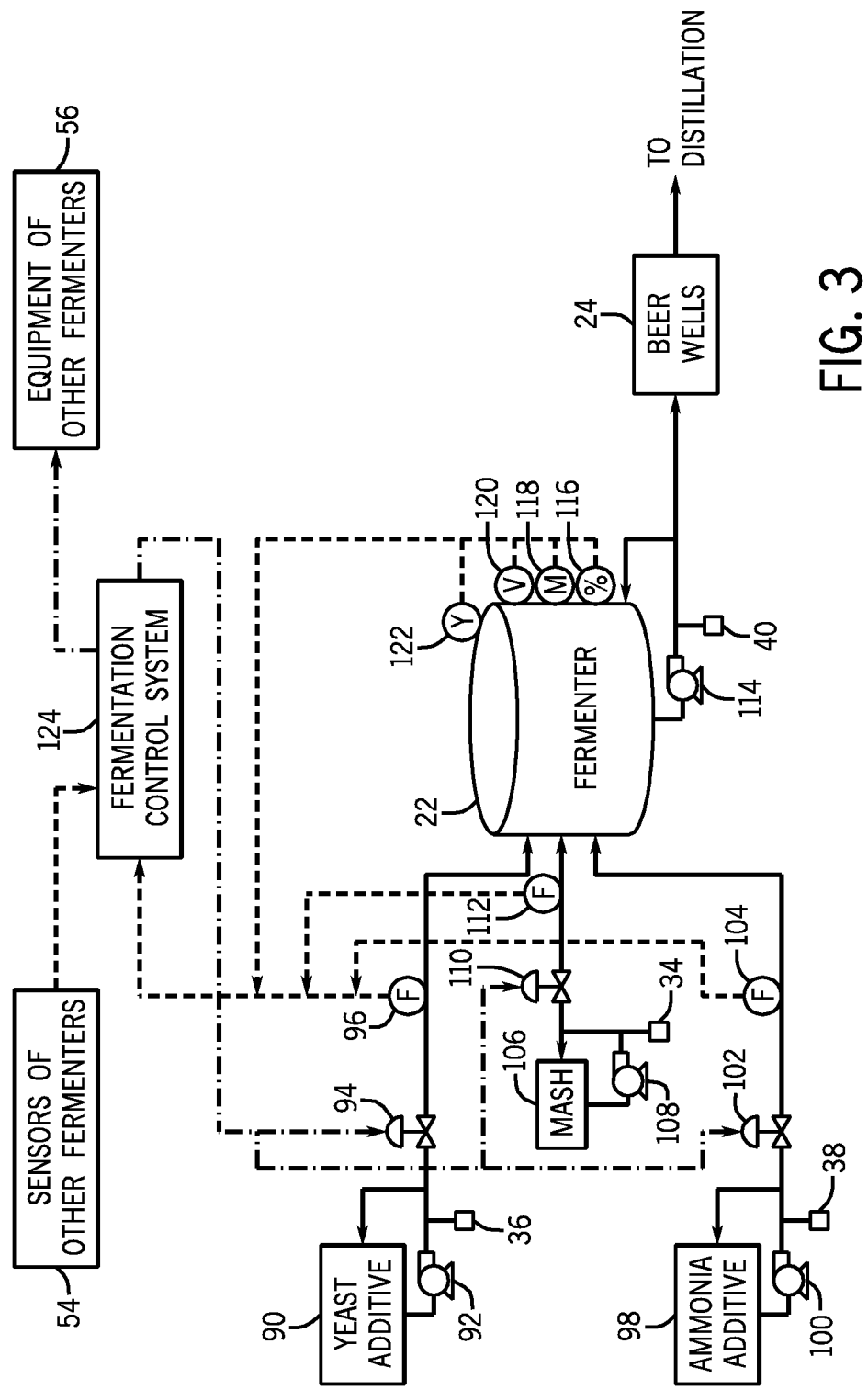
FIG. 3 is a diagrammatical representation of certain functional components of a single fermenter of the biofuel production plant of FIG. 1 configured to implement an exemplary method of controlling a fermentation process.

FIG. 3 is a more detailed process flow diagram of components of a single fermenter 22 of the biofuel production plant 10 of FIG. 1, illustrating various sensors and valves of an embodiment of the yeast additive system 18 and the ammonia additive system 20. Turning first to the yeast additive system 18, it may include a yeast additive tank 90 to store the yeast additive. Next, a yeast additive pump 92 may be used to both recirculate the yeast additive and transfer the yeast additive to the fermenter 22. A yeast additive control valve 94 may be located on the discharge of the yeast additive pump 92 to automatically control the flow rate of the yeast additive. Further, a yeast additive flow meter 96 may be used to measure the flow rate of the yeast additive to the fermenter 22. Thus, the flow rate of the yeast additive may be a manipulated variable (MV) of the process management and control module 52. For example, the yeast additive may be added to the fermenter 22 at a fixed rate for a specified time, such as between approximately 4 hours to 6 hours. Alternatively, the yeast additive may be added in a linear fashion with respect to a mash feed flow rate.

The ammonia additive system 20 may be configured similar to the yeast additive system 18. Specifically, the ammonia additive system 20 may include an ammonia additive tank 98 to store the ammonia additive. Next, an ammonia additive pump 100 may be used to both recirculate the ammonia additive and transfer the ammonia additive to the fermenter 22. An ammonia additive control valve 102 may be located on the discharge of the ammonia additive pump 100 to automatically control the flow rate of the ammonia additive. Further, an ammonia additive flow meter 104 may be used to measure the flow rate of the ammonia additive to the fermenter 22. Thus, the flow rate of the ammonia additive may also be an MV of the process management and control module 52. In certain embodiments, the inclusion of two additional MV's, namely the yeast and ammonia flow rates, may help improve overall control of the fermentation process. For example, not only may dextrose concentration be controlled to an end point, but total sugars at a fermenter drop may be controlled. In addition, the yeast and ammonia flow rate MV's may be available both during and after a fill cycle of the fermenter 22, providing improved process control. Other MV's, such as enzyme addition or fermenter temperature, may only be available for control during or after the fill cycle, but not both, as described more fully in U.S. patent application Ser. No. 11/928,344, incorporated by reference herein.

Similarly, the mash preparation system 16 may include a mash tank 106 to store the mash during preparation. Next, a mash pump 108 may be used to both recirculate the mash and transfer the mash to the fermenter 22. A mash control valve 110 may be located on the discharge of the mash pump 108 to automatically control the flow rate of the mash. Further, a mash flow meter 112 may be used to measure the flow rate of the mash to the fermenter 22.

Regarding the sequence of steps during the fermenter batch, in certain embodiments, the mash 106 is injected into the fermenter 22 during a fill cycle. The yeast additive 90 and/or the ammonia additive 98 may also be injected into the fermenter 22 during the fill cycle. Other additives may also be injected during the fill cycle. In other embodiments, the yeast additive 90 and/or the ammonia additive 98 may be injected into the fermenter 22 after the fill cycle is complete or before the fill cycle begins. In further embodiments, a first portion of the yeast additive 90 and/or the ammonia additive 98 may be injected during the fill cycle and a second portion of the yeast additive 90 and/or the ammonia additive 98 may be injected after the fill cycle is complete. Thus, addition of the yeast additive 90 and/or the ammonia additive 98 is not limited to only during the fill cycle of the fermenter batch.

In certain embodiments, the fermenter 22 may have a fermenter pump to both recirculate the fermenter contents and transfer the fermenter contents to the beer wells 24. In addition, the fermenter 22 may include one or more sensors. For example, the fermenter 22 may include a percentage fill sensor 116, which may provide a value between approximately 0 percent to 100 percent. The fermenter 22 may include a mass fill sensor 118, which may indicate the number of kilograms contained in the fermenter 22. Similarly, the fermenter 22 may include a volumetric fill sensor 120, which may indicate the number of liters contained in the fermenter 22. Finally, the fermenter 22 may include a yeast activation sensor 122, which may be a component of yeast activation monitoring 74, to provide yeast activity data of the fermenter contents. In further embodiments, the mash preparation system 16, the yeast additive system 18, the ammonia additive system 20, and the fermenter 22 may include additional sensors and/or equipment other than what is described above. For example, the fermenter 22 may include a pH probe that indicates the pH value of the fermenter contents.

As shown in FIG. 3, the output from all of the sensors (indicated by the dashed lines) is transmitted to a fermentation control system 124, which may be a part of the process management and control module 52. Although shown as interconnecting, the signals from the sensors may pass through separate electrical conductors to an interface and then to the control system 124. In addition, output signals from the control system 124 are transmitted to the control valves 94, 100, and 102 (indicated by the dashed and dotted lines) to achieve desired flow rates. Again, although the lines are shown interconnecting, the signals may pass from the control system 124, through an interface, and then through separate electrical conductors to each of the control valves 94, 100, and 102. Alternatively, wireless technology may be used to replace any or all of the electrical conductors. In addition, data from the sensors 54 of other fermenters may be transmitted to the control system 124 and output signals transmitted to the control valves or other equipment 56 of the other fermenters. As discussed above, the control system 124 may operate in a closed-loop manner.

The desired flow rates of yeast or ammonia determined by the fermentation control system 124 may remain at a fixed value or change during the fermenter batch. For example, yeast or ammonia may be added to the fermenter 22 at a first flow rate for a first time period and then added at a second flow rate for a second time period. In various embodiments, the desired flow rates may be determined and adjusted by the fermentation control system 124 to achieve particular goals, such as, but not limited to, increasing yeast growth, increasing ethanol production, increasing fermenter yield, or maintaining the pH value within a specified range. For example, if the pH value of the fermenter contents is below a threshold or too acidic, the fermentation control system 124 may increase the flow rate of ammonia additive 98 to the fermenter 22. In other embodiments, the desired flow rates may be functions of the volumetric, mass, or percentage fill of mash in the fermenter 22 as measured by the volumetric fill sensor 120, mass fill sensor 118, or percentage fill sensor 116 respectively. In some embodiments, the desired flow rates may be functions of yeast activity feedback, as measured by fermenter samples 40, measured by the yeast activation sensor 122, measured by yeast activation monitoring 74, or based on the yeast activation model 70. In further embodiments, the desired flow rates may be a function of the mash flow rate as measured by the mash flow meter 112.

Figure 4:
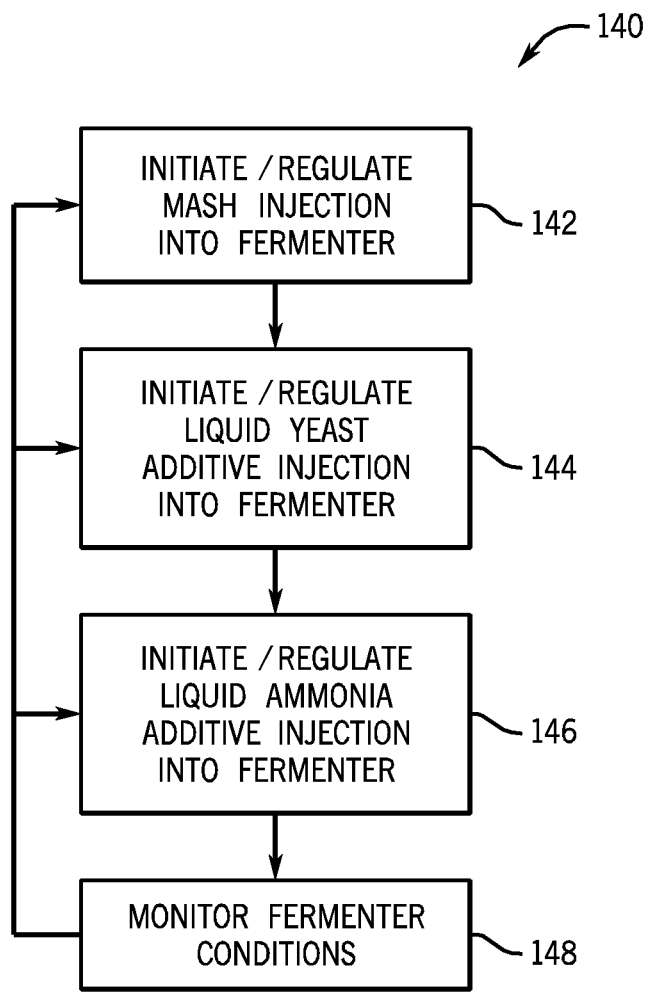
FIG. 4 is a flowchart of an exemplary method for controlling a fermentation process.

FIG. 4 is a flowchart of an exemplary method 140 for controlling a fermentation process that may be implemented by the fermentation control system 124. An embodiment of the invention may be embodied in the form of computer-implemented processes and apparatuses for practicing those processes. Embodiments of the present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing embodiments of the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via wireless transmission, wherein when the computer program code is loaded into and executed by a computer, the computer becomes an apparatus for practicing embodiments of the invention. When implemented on a general-purpose processor, the computer program code segments configure the processor to create specific logic circuits. A technical effect of the method 140 may include, among others, the controlling of the fermentation processes in a biofuel production plant 10 via the yeast additive system 18 and/or the ammonia additive system 20.

Specifically, the fermentation control system 124 may include computer code disposed on a computer-readable storage medium or a process controller that includes such a computer-readable storage medium. The computer code may include instructions for controlling the flow rates of yeast and/or ammonia to one or more fermenters 20 in a biofuel production plant 10. In other embodiments, the computer code may include additional instructions. For example, the code may include instructions for determining an economic cost of energy utilized within the yeast additive system 18 and/or ammonia additive system 20 and determining an economic value of products produced by the biofuel production plant 10. In other embodiments, the instructions for determining optimal target values for the flow rates of the yeast and/or ammonia may be based on the economic cost and economic value determinations. In further embodiments, the code may include instructions for measuring the operating variables using process instruments or for cyclically repeating certain instructions.

Returning to FIG. 4, each fermenter 22 of several operating in parallel may be at different steps of the method 140 depending on the progress of the fermenter batches. First, step 142 represents the initiation and/or regulation of the injection of mash from the mash preparation system 16 to the fermenter 22. For example, referring to FIG. 3, the mash control valve 110 may be opened and the mash pump 108 turned on to transfer the mash to the fermenter 22. The mash control valve 110 may be throttled to achieve a desired mash flow rate, as measured by the mash flow meter 112. When the desired amount of mash is transferred to the fermenter 22, the mash control valve 110 may be closed and the mash pump 108 turned off or left circulating the contents of the mash tank 106. All of these steps may be controlled by the fermentation control system 124 in a closed-loop manner. Next, step 144 represents the initiation and/or regulation of the injection of liquid yeast additive by the fermentation control system 124. As with the mash, the yeast additive pump 92, yeast additive control valve 94, and the yeast additive flow meter 96 may be used to initiate, regulate, and terminate the transfer of yeast additive to the fermenter 22 in a closed-loop manner. In embodiments that only include the ammonia additive system 20 and use dry yeast instead of cream yeast, step 144 is omitted. Next, step 146 represents the initiation and/or regulation of the injection of liquid ammonia additive by the fermentation control system 124. As with the liquid yeast additive, the ammonia additive pump 100, ammonia additive control valve 102, and the ammonia additive flow meter 104 may be used to initiate, regulate, and terminate the transfer of ammonia additive to the fermenter 22 in a closed-loop manner. In embodiments that only include the yeast additive system 18 and use urea instead of ammonia, step 146 is omitted. In step 148, the fermentation control system 124 monitors appropriate conditions of the fermenter 22, such as volumetric, mass, or percentage fill, yeast activity, temperature, pH value, ethanol concentration, and so forth. Based on these monitored conditions, the fermentation control system 124 may return to one or more of steps 142, 144, and/or 146 to further regulate mash, yeast, and/or ammonia injection to the fermenter 22 to achieve certain goals of the fermentation process.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for controlling a batch fermentation process, comprising:
   injecting a mash into a fermenter during a fill cycle of the batch fermentation process;
   receiving process data from a plurality of fermenter sensors, one or more liquid yeast sensors, and one or more liquid ammonia sensors, wherein:
   the plurality of fermenter sensors are configured to measure the process data comprising an ethanol concentration, liquid level, temperature, pH value, yeast properties, and ammonia properties of the mash inside the fermenter;

the one or more liquid yeast sensors are configured to detect a first flow rate of a liquid yeast additive being provided into the fermenter; and the one or more liquid ammonia sensors are configured to detect a second flow rate of a liquid ammonia additive being provided into the fermenter;

determining a current activity of a yeast in the fermenter based on the process data and a yeast activation model;

adjusting the first flow rate of the liquid yeast additive being provided into the fermenter during the fill cycle and after the fill cycle ends based upon a comparison of the current activity of the yeast in the fermenter to a threshold; and adjusting the second flow rate of the liquid ammonia additive being provided into the fermenter during the fill cycle and after the fill cycle ends based upon the comparison of the current activity of the yeast in the fermenter to the threshold.

2. The method of claim 1, wherein the yeast activation model is configured to determine the current activity of the yeast in the fermenter based on one or more empirical models, one or more inferential models, laboratory data, or any combination thereof.

3. The method of claim 1, wherein the first flow rate of the liquid yeast additive and the second flow rate of the liquid ammonia additive are further adjusted as a function of volume, mass, or percentage fill of the mash in the fermenter.

4. The method of claim 1, further comprising adjusting the first flow rate of the liquid yeast additive throughout the entire batch process based on the current activity of the yeast in the fermenter.

5. The method of claim 1, further comprising adjusting the second flow rate of the liquid ammonia additive throughout the entire batch process based on the current activity of the yeast in the fermenter.

6. The method of claim 1, wherein the first flow rate of the liquid yeast additive is adjusted while the mash is injected into the fermenter.

7. The method of claim 1, wherein the second flow rate of the liquid ammonia additive is adjusted while the mash is injected into the fermenter.

8. The method of claim 1, wherein the plurality of fermenter sensors are disposed in the fermenter, the one or more liquid yeast sensors are disposed at a first inlet configured to supply the liquid yeast additive to the fermenter, and the one or more liquid ammonia sensors are disposed at a second inlet configured to supply the liquid ammonia additive to the fermenter.

9. The method of claim 1, wherein adjusting the first flow rate comprises increasing the first flow rate in response to the current activity being less than the threshold.

10. The method of claim 1, wherein adjusting the first flow rate comprises decreasing the first flow rate in response to the current activity being greater than the threshold.

11. A system for controlling a batch fermentation process, comprising:
a fermenter configured to receive a mash and to ferment the mash during a batch process;
a plurality of fermenter sensors configured to measure process data comprising a yield of the fermenter and properties of the mash in the fermenter, wherein the properties of the mash in the fermenter comprise a volume, mass, percentage fill, ethanol concentration, liquid level, temperature, pH value, yeast properties, and ammonia properties;

one or more liquid yeast sensors configured to detect a first flow rate of a liquid yeast additive being provided into the fermenter;
one or more liquid ammonia sensors configured to detect a second flow rate of a liquid ammonia additive being provided into the fermenter;
a liquid yeast additive system configured to inject a liquid yeast additive into the fermenter during a fill cycle of the batch fermentation process and after the fill cycle ends;
a liquid ammonia additive system configured to inject a liquid ammonia additive into the fermenter during the fill cycle and after the fill cycle ends; and
a control system communicatively coupled to the liquid yeast additive system and the liquid ammonia additive system and configured to:
determine a current activity of the yeast in the fermenter based on the process data and a yeast activation model; and
regulate the injection of the liquid yeast additive and the liquid ammonia additive based upon a comparison of the current activity of the yeast in the fermenter to a threshold activity.

12. The system of claim 11, further comprising a mash injection system configured to inject mash into the fermenter.

13. The system of claim 11, further comprising a mash pump configured to circulate the mash inside the fermenter.

14. The system of claim 11, wherein regulating the injection of the liquid yeast additive and the liquid ammonia additive comprises adjusting the first flow rate and the second flow rate.

15. The system of claim 11, further comprising a yeast additive pump and a yeast additive tank comprising the liquid yeast additive, wherein the yeast additive tank is fluidly coupled to the fermenter, and wherein the yeast additive pump is configured to recirculate the liquid yeast additive in the yeast additive tank.

16. The system of claim 11, further comprising an ammonia additive pump and an ammonia additive tank comprising the liquid ammonia additive, wherein the ammonia additive tank is fluidly coupled to the fermenter, and wherein the ammonia additive pump is configured to recirculate the liquid ammonia additive in the ammonia additive tank.

17. A non-transitory computer-readable medium comprising computer-executable instructions configured to, when executed, cause a processor to:
receive process data from a plurality of fermenter sensors, one or more liquid yeast sensors, and one or more liquid ammonia sensors, wherein:
the plurality of fermenter sensors are configured to measure the process data comprising an ethanol concentration, liquid level, temperature, pH value, yeast properties, and ammonia properties of the mash inside the fermenter;
the one or more liquid yeast sensors are configured to detect a first flow rate of a liquid yeast additive being provided into the fermenter; and
the one or more liquid ammonia sensors are configured to detect a second flow rate of a liquid ammonia additive being provided into the fermenter;
determine a current activity of a yeast in the fermenter based on the process data and a yeast activation model;
send a first command to a first valve to adjust the first flow rate of the liquid yeast additive being provided into the fermenter during the fill cycle and after the fill cycle ends based upon a comparison of the current activity of the yeast in the fermenter to a threshold activity; and send a second command to a second valve to adjust the second flow rate of the liquid ammonia additive being provided into the fermenter during the fill cycle and after the fill cycle ends based upon the comparison of the current activity of the yeast in the fermenter to the threshold activity.

18. The non-transitory computer-readable medium of claim 17, wherein the first command causes the first valve to decrease the first flow rate of liquid yeast additive in response to the current activity of the yeast in the fermenter being greater than the threshold activity.

19. The non-transitory computer-readable medium of claim 17, wherein the first command causes the first valve to increase the first flow rate of liquid yeast additive in response to the current activity of the yeast in the fermenter being less than the threshold activity.

20. The non-transitory computer-readable medium of claim 17, wherein the computer-executed instructions are further configured to cause the processor to send a third command to the second valve to adjust the second flow rate of the liquid ammonia additive being provided into the fermenter during the fill cycle and after the fill cycle ends based upon the pH value of the mash being below a threshold acidity.

* * * * *